United States Patent
Olson et al.

(10) Patent No.: US 8,116,547 B2
(45) Date of Patent: Feb. 14, 2012

(54) SIGNAL TO NOISE RATIO IN DIGITAL PATHOLOGY IMAGE ANALYSIS

(75) Inventors: Allen Olson, San Diego, CA (US); Ole Eichhorn, Westlake Village, CA (US)

(73) Assignee: Aperio Technologies, Inc., Vista, CA (US)

(*) Notice: Subject to any disclaimer, the term of this patent is extended or adjusted under 35 U.S.C. 154(b) by 0 days.

(21) Appl. No.: 13/259,562

(22) PCT Filed: Dec. 10, 2010

(86) PCT No.: PCT/US2010/059861
§ 371 (c)(1),
(2), (4) Date: Sep. 23, 2011

(87) PCT Pub. No.: WO2011/072211
PCT Pub. Date: Jun. 16, 2011

(65) Prior Publication Data
US 2012/0014576 A1    Jan. 19, 2012

Related U.S. Application Data

(60) Provisional application No. 61/285,867, filed on Dec. 11, 2009.

(51) Int. Cl.
*G06K 9/00* (2006.01)
(52) U.S. Cl. .......................... 382/128; 382/133; 382/284
(58) Field of Classification Search .................. 382/128, 382/133, 283, 284, 305; 358/1.5, 1.15; 348/345
See application file for complete search history.

(56) References Cited

U.S. PATENT DOCUMENTS

| | | | | |
|---|---|---|---|---|
| 7,428,324 | B2 * | 9/2008 | Crandall et al. | 382/128 |
| 7,602,524 | B2 * | 10/2009 | Eichhorn et al. | 358/1.5 |
| 7,912,259 | B2 | 3/2011 | Arditi et al. | |

(Continued)

FOREIGN PATENT DOCUMENTS

EP    0610916    8/1994

(Continued)

OTHER PUBLICATIONS

PCT/US2010/059861, PCT/ISA/220—International Search Report, Dated: Jul. 27, 2011.
PCT/US2010/059861, PCT/ISA/237—Written Opinion of the International Searching Authority, Dated: Jul. 27, 2011.

*Primary Examiner* — Duy M Dang
(74) *Attorney, Agent, or Firm* — Pattric J. Rawlins; Procopio Cory Hargreaves & Savitch LLP (57) ABSTRACT

A digital slide analysis system comprises an algorithm server that maintains or has access to a plurality of image processing and analysis routines. The algorithm server additionally has access to a plurality of digital slide images. The algorithm server executes a selected routine on an identified digital slide and provides the resulting data. Prior to the application of selected routine, the system employs a digital pre-processing module to create a metadata mask that reduces undesirable image data such that the image data processed by the selected routine has an improved signal to noise ratio. The pre-processing module uses a classifier that may be implemented as a pattern recognition module, for example. Undesirable image data is therefore excluded from the image data that is processed by the digital pathology image processing and analysis routine, which significantly improves the digital pathology image analysis.

15 Claims, 3 Drawing Sheets

U.S. PATENT DOCUMENTS

| | | | |
|---|---|---|---|
| 2004/0252875 A1* | 12/2004 | Crandall et al. | 382/133 |
| 2006/0007345 A1* | 1/2006 | Olson et al. | 348/345 |
| 2007/0020697 A1 | 1/2007 | Cualing et al. | |
| 2007/0036462 A1* | 2/2007 | Crandall et al. | 382/284 |
| 2008/0166035 A1 | 7/2008 | Qian et al. | |

FOREIGN PATENT DOCUMENTS

JP    2008-508972    3/2008

* cited by examiner

SIGNAL TO NOISE RATIO IN DIGITAL PATHOLOGY IMAGE ANALYSIS

This application is a continuation of PCT application PCT/US10/059,861, filed Dec. 10, 2010, which claims benefit of U.S. Provisional Patent Application 61/285,867, filed Dec. 11, 2009.

BACKGROUND

1. Field of the Invention

The present invention generally relates to digital microscopy and more specifically relates to the processing and analysis of digital slides.

2. Related Art

In the growing field of digital pathology, computer assisted image analysis is becoming increasingly important to assist pathologists with image analysis. One problem with conventional digital pathology image analysis systems is that the image data processed by a set of image processing instructions typically includes a significant amount of undesirable image data (i.e., low signal (desired image data) to noise (undesired image data) ratio). This undesirable image data is necessarily processed by the conventional digital pathology image analysis systems because those systems process all image data received for analysis. The image data received for analysis includes the undesirable image data because an operator is unable to efficiently exclude undesirable image data prior to image analysis by the conventional digital pathology image analysis systems. Some attempts to solve the low signal to noise ratio problem have resulted in extremely complicated digital pathology image processing algorithms that are also extremely limited in their application due the inclusion of image processing instructions with the analysis instructions. Therefore, there is a need in the industry for an improved digital pathology image analysis system that solves the problems of the conventional systems and addresses the inadequacies of previously attempted solutions.

SUMMARY

A system and method for processing and analyzing digital pathology images ("digital slides") is provided. The system comprises an algorithm server that maintains or has access to a plurality of digital pathology image processing and analysis routines. The algorithm server additionally has access to a plurality of digital slides. The algorithm server executes one or more selected digital pathology image processing and analysis routines on image data from a digital slide and provides the resulting analysis data. Prior to the application of a digital pathology image processing and analysis routine, the system employs a digital pre-processing module to mask undesirable image data such that only image data desired to be processed by the digital pathology image processing and analysis routine is provided to the algorithm. The pre-processing module uses a classifier that may be implemented as a pattern recognition module, for example. Undesirable image data is therefore excluded from the image data that is processed by the digital pathology image processing and analysis routine, which significantly improves the signal to noise ratio in the digital pathology image analysis. Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide a framework for processing and analysis of digital slide images. The system comprises an algorithm server that pre-processes a digital slide image (or portion thereof) using a classifier to create a metadata mask that, when applied to the digital slide image, produces the desired image data with an improved signal to noise ratio. Using the improved signal to noise ratio image data from the digital slide image, the algorithm server executes image processing instructions (referred to herein as "algorithms," "routines," and "sub-routines") to generate an analysis of the desired image data. For example, one method disclosed herein allows a user to identify a digital slide image (or a sub-region thereof), a classifier, and an algorithm to be used in the processing and analysis of the image. The server then applies the classifier to the digital slide image (or sub-region thereof) to generate improves signal to noise ratio image data that is then analyzed using the selected algorithm. The results of the analysis by the algorithm may be provide to the screen, to a file, to a database, or otherwise presented, captured and/or recorded. Certain parameters may also be provided by the user or obtained from a data file corresponding to the particular algorithm to constrain the processing and analysis called for in the algorithm. These parameters may include the metadata mask that defines the desired image data to be analyzed.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
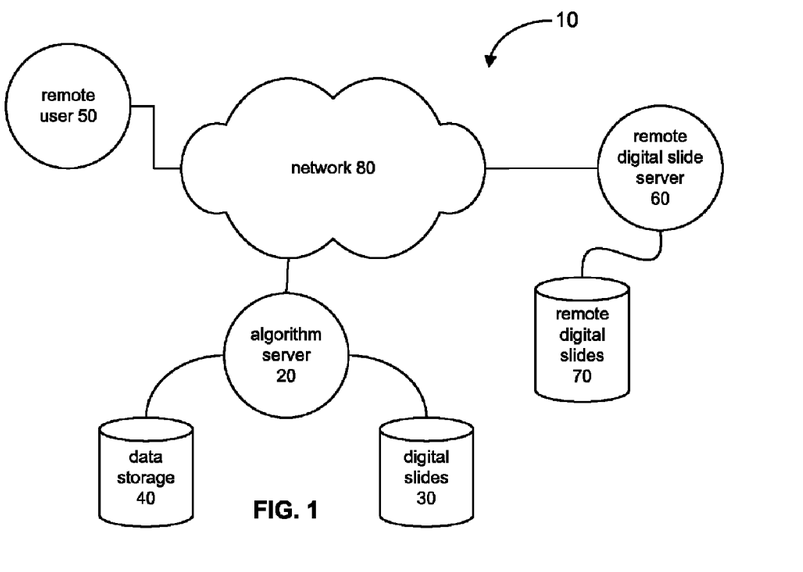
FIG. 1 is a network diagram illustrating an example system for image processing and analysis according to an embodiment of the present invention.

FIG. 1 is a network diagram illustrating an example system 10 for image processing and analysis according to an embodiment of the present invention. In the illustrated embodiment, the system 10 comprises an algorithm server 20 that is communicatively linked with one or more remote users 50 and one or more remote image servers 60 via a network 80. The algorithm server is configured with a data storage area 40. In at least a portion of the data storage area 40 a plurality of local digital slide image files 30 are stored. Although the illustrated embodiment shows the digital slide image files in a separate data storage area, those skilled in the art will understand that the digital slides 30 may be stored on a variety of non-transitory media that collectively comprise data storage area 40. Additionally, the data storage area 40 preferably comprises information related to the processing of digital image files, for example it may store certain analysis routines, parameters, and procedural lists of analysis routines and associated parameters ("macros"), among other types of data. The local digital slide image files 30 and remote digital slide image files 70 are preferably digital slides of the type created by the ScanScope® Microscope Slide Scanner developed by Aperio Technologies, Inc. The ScanScope® product is described in detail in U.S. Pat. No. 6,711,283, which is incorporated by reference herein in its entirety.

The remote image server 60 is preferably configured with a data storage area having a plurality of digital slide image files 70 that are considered remote from the algorithm server. In one embodiment, the algorithm server 20 may access the remote digital slide images 70 via the network 80. The remote user 50 may comprise a web browser, an imagescope viewer, a scanscope console, an algorithm framework, or some other client application or front end that facilitates a user's interaction with the algorithm server 20. The network 80 can be a local area network ("LAN"), a wide area network ("WAN"), a private network, public network, or a combination of networks such as the Internet.

Figure 2:
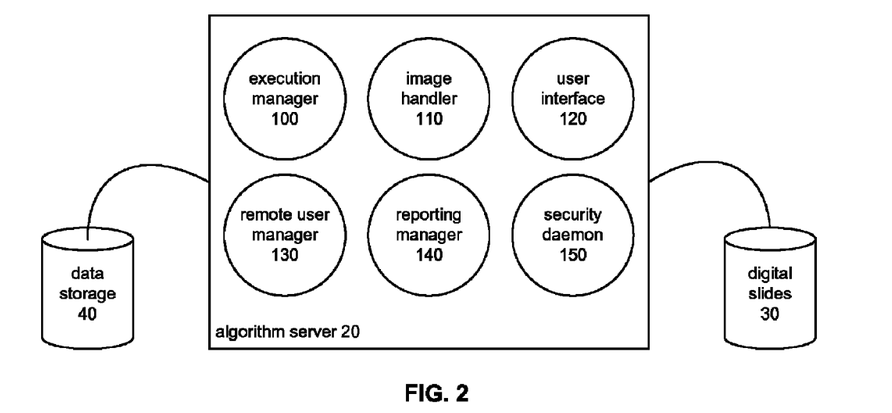
FIG. 2 is a block diagram illustrating an example algorithm server according to an embodiment of the present invention.

FIG. 2 is a block diagram illustrating an example algorithm server 20 according to an embodiment of the present invention. In the illustrated embodiment, the algorithm server 20 comprises an execution manager 100, an image handler 110, a user interface 120, a remote user manager 130, a reporting manager 140, and a security daemon 150. The algorithm server is also configured with a data storage area 40 and a plurality of local image files 30 and a plurality of remote image files 70. Preferably, the local and remote image files are digital slides.

The execution manager 100 handles the process of executing an algorithm to conduct image analysis or other types of analysis on a digital slide. The execution manager 100 can be in communication with the other components of the algorithm server in order to process the image analysis requests from one or more local or remote users. For example, the execution manager 100 is configured to receive an instruction from a user to run a particular algorithm on a certain digital slide. The execution manager 100 is also configured to collect parameter data from the user that will be used by the algorithm during execution. The parameters may define a sub-region of the digital slide to be processed by the algorithm and/or may define certain threshold values or provide other data elements to constrain the algorithm during execution.

The execution manager 100 is communicatively coupled with the image handler 110 in order to obtain the digital slide (or portion thereof) for analysis and processing pursuant to the particular algorithm. Because digital slides are such large files (10-15 GB uncompressed), a specialized image handler 110 is employed to efficiently and quickly obtain image data for processing. Advantageously, the image handler 110 can obtain image data from digital slides that are stored either locally (image files 30) or remotely (image files 70). Additionally, the image handler 110 provides the digital slide image in a standard format by decompressing the stored digital slide image from various compression formats including JPEG, JPEG2000, and LZW formats.

Another function of the image handler 110 is to provide the image data from a digital slide at the proper level of magnification. For example, an image may be stored in at a native resolution of 40× but a resolution of 20× is called for by the algorithm. The image handler 110 can downsample the native resolution and deliver the image data at a resolution of 20× to the execution manager 100. Such ability provides a significant advantage in speed for algorithms that initially process an image at a low resolution where objects of interest are detected and subsequently process the image at a high resolution where the analysis of those sub-regions containing the identified objects of interest is carried out. For example, the amount of image data to be processed in a 40× image is four times the amount of image data to be processed in a 20× image, so an algorithm which processes a 40× image at a resolution of 20× can run four times faster.

Another function of the image handler 110 is to apply a pre-processing classifier to the digital slide image data and generate a metadata mask that, when applied to the digital slide image, produces the desired digital slide image data with an improved signal to noise ratio for analysis by the algorithm. The image handler 110 may apply the pre-processing classifier to the digital slide image at its native resolution or at another resolution. In one embodiment, the image handler 110 applies the pre-processing classifier to the digital slide image at its native (i.e., scanned) resolution to create the metadata mask and then scales the metadata mask to the desired image resolution and applies the metadata mask to image data from the digital slide at the desired resolution. In an alternative embodiment, the image handler 110 applies the pre-processing classifier to the digital slide image at a resolution other than the native resolution. For example, a digital slide image file may advantageously include a plurality of complete images, each complete image at a different resolution. In such an example digital slide image file, a baseline image corresponds to the scanned resolution and a plurality of intermediate images each at successively lower resolutions are also included in the digital slide image file. In one embodiment, the lowest resolution image in the digital slide image file may be a thumbnail image.

In accordance with this function, the image handler 110 accesses image data from a data storage area 30 that includes a plurality of digital slide images. The image handler 110 analyzes the image data using the classifier to identify image data that corresponds to a desired characteristic that is associated with the classifier. Image data this is not identified as corresponding to the desired characteristic is included in a metadata mask that defines one or more contiguous regions of the image data. Accordingly, the metadata mask may be a series of X,Y locations in the image data that collectively define one or more contiguous regions that do not include the desired characteristic. The metadata mask can be stored in data storage area 40 as a string or a vector or some other convenient format for such data as will be understood by those having skill in the art.

The user interface 120 preferably provides the user with a simple and easy to use format for interacting with the execution manager 100 in order to identify the algorithm to execute and the digital slide to be analyzed. Additionally the user interface 120 can efficiently collect parameter data from a user prior to execution of an algorithm. The user interface 120 also allows a user to create a macro comprising a plurality of algorithms and associated parameters.

The remote user manager 130 preferably manages the connection and communication with a user that is accessing the algorithm server 20 through a network connection. The remote user manager 130 is also configured to receive requests from network based users and programs, and to process those requests in real time or as a scheduled batch.

The reporting manager 140 is preferably configured to receive output and processing results from the execution manager 100 as an algorithm executes and generates data or other output. The reporting manager may also access output files after an algorithm is finished processing and then restructure the data in the output file into a standard report format. Additional reporting capabilities may also be provided by the reporting manager 140, as will be understood by those having skill in the art.

The security daemon 150 advantageously handles image processing requests that originate from a network based user or program. The security daemon 150 receives all incoming network requests and examines those requests to determine if they are seeking to process an image with an algorithm. If so, the security daemon 150 is configured to validate the request and if the request is valid, then the security daemon 150 passes the request off to the execution manager 150 for processing.

In one embodiment, the data storage area 40 may contain a plurality of algorithms that can be executed in order to analyze digital slide images. Additionally, the data storage area 40 may also contain a plurality of sub-routines that are commonly performed or often included in image processing algorithms. Advantageously, these common sub-routines can be dynamically linked into an algorithm at runtime so that the algorithm development effort is simplified. Additionally, the data storage area 40 may also comprise a plurality of macros, where a macro comprises a linear or parallel sequence of processing images with algorithms to achieve a desired analysis. A macro may also comprise parameter data to define subregions of images where appropriate and provide variables to constrain the image processing.

Figure 3A:
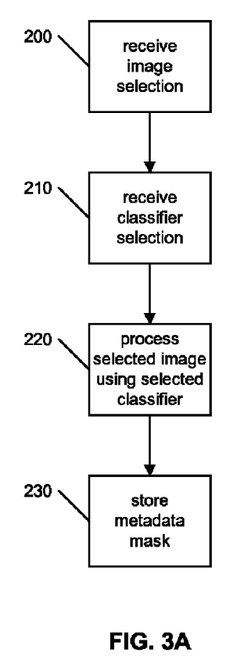
FIG. 3A is a flow diagram illustrating an example process for creating a metadata mask according to an embodiment of the present invention.

FIG. 3A is a flow diagram illustrating an example process for creating and storing a metadata image mask according to an embodiment of the present invention. In one embodiment, this process may be carried out by the previously described algorithm server 20. Initially, in step 200 an image selection is received. The image selection identifies a digital slide image stored locally or remotely in, e.g., data storage 40, digital slides 30, or remote digital slides 70. The image selection may also include additional information including user annotation information and/or subregion identification information. In one embodiment, the user annotation data describes a subregion of the digital slide image containing the desired image data (along with undesired image data) for processing with the selected algorithm.

Next, in step 210 the classifier selection is received. There can be a variety of classifiers that can be used when pre-processing the image data to be analyzed by the selected algorithm. For example, a pattern matching utility can be utilized as a classifier that identifies desired patterns in the image data. Other types of classifiers may identify desired color features, desired anomalous features, desired cellular structures, or any other desired feature in the digital slide image data. Once the desired classifier has been selected, the selected digital slide image (or subregion thereof) is processed using the selected classifier to create a metadata mask. Advantageously, the classifier identifies the desired image data in the digital slide image data (or subregion thereof) and produces a metadata mask that, when applied to the digital slide image (or subregion thereof), results in only the desired image data (e.g., the image data identified by the classifier) from the digital slide image (or subregion thereof) and thus the resulting image data has a significantly higher signal to noise ratio than can be produced by conventional systems.

After the metadata mask is created, it is stored in volatile or persistent memory for immediate or later use by the system to produce the desired image data from the digital slide image (or subregion thereof). For example, the desired image data can be immediately provided to a selected algorithm for analysis. Also, the metadata mask can be used later to obtain the same desired image data from the selected digital slide image and provided at that time to the same or a different selected algorithm for analysis. One significant advantage of this is that the same desired image data can be serially processed by a plurality of algorithms to generate a comprehensive analysis of only the desired image data such that the resulting analysis is significantly more accurate due to the improved signal to noise ratio in the image data that was analyzed by the algorithm.

Figure 3B:
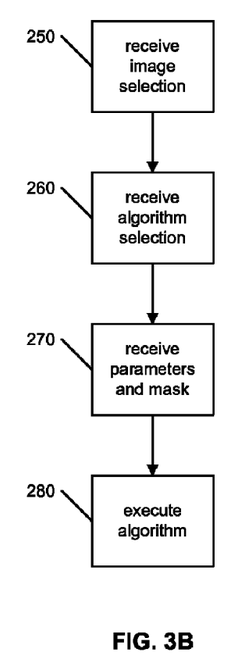
FIG. 3B is a flow diagram illustrating an example process for executing an image processing algorithm according to an embodiment of the present invention.

FIG. 3B is a flow diagram illustrating an example process for executing an image processing algorithm according to an embodiment of the present invention. In one embodiment, this process may be carried out by the previously described algorithm server 20. Initially, in step 250, the execution manager receives an image selection. The image selection can be for a particular digital slide, or an identified sub-region thereof. Advantageously, the image selection may also be the result of the process described with respect to FIG. 3B such that the selected digital slide image is first processed by a desired classifier so that the resulting image data has an improved signal to noise ratio, which results in improved results from the analysis by the selected algorithm. Next, in step 260, the execution manager receives a selection for the algorithm to be run. There may in fact be more than one algorithm, or the execution manager may receive the selection of a macro that comprises several algorithms. In step 270, the execution manager receives parameter data necessary to run the algorithm(s). Advantageously, the execution manager may query the algorithm or check a corresponding data file to determine what parameter data will be required to run the algorithm(s).

In one embodiment, the parameter data may include an identification of a metadata image mask, e.g., generated by the process described with respect to FIG. 3B and stored in memory. As previously discussed, the metadata image mask defines the desirable area of image data to be processed by the selected algorithm. The metadata image mask can be created by a variety of different types of classifiers, for example a pattern recognition classifier. The classifier pre-processes the selected image to determine the metadata image mask such that the defined area of desired image data includes all of the image data matching a particular pattern or including a desired characteristic. The metadata mask may define a contiguous portion of image data from the selected digital slide image or it may be a plurality of disconnected portions of image data from the selected digital slide image.

Finally, in step 280, after the image has been selected and the algorithm selected and the parameter data provided, the execution manager runs the algorithm on only the desired image data produced by the metadata mask and preferably provides any output to an output file, the screen, a database, or other display or storage facility.

Figure 4:
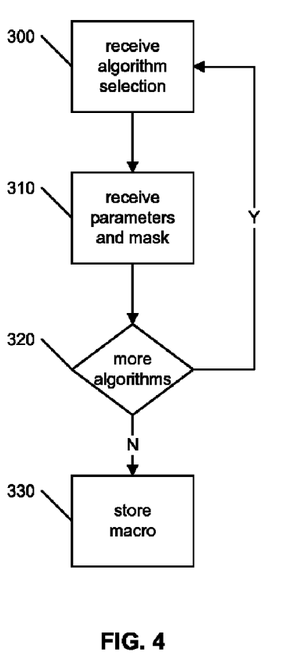
FIG. 4 is a flow diagram illustrating an example process for creating an image processing macro according to an embodiment of the present invention.

FIG. 4 is a flow diagram illustrating an example process for creating an image processing macro according to an embodiment of the present invention. Initially, in step 300, the execution manager receives a selection for the first algorithm to be run as part of the macro. Next, in step 310, the execution manager receives the parameter data that corresponds to the selected algorithm. The parameter data may advantageously include a metadata image mask. In some cases, all of the parameter may not be provided when the macro is created. Advantageously, the execution manager can collect a partial set of parameter data and then when the macro is run, the execution manager can prompt the user for the needed additional parameter data. For example, the user or program requesting the macro be run will also have to identify the digital slide to be processed, and optionally the subregion of the image on which the algorithm will operate.

Once the algorithm selection and the parameter data have been collected, the user is prompted to determine in step 320 if there are more algorithms to be included in the macro. If so, then the process loops back to collect the algorithm selection and parameter data as described immediately above. If the macro definition is complete, then in step 330 the macro is stored in persistent data storage for later retrieval and execution.

Figure 5:
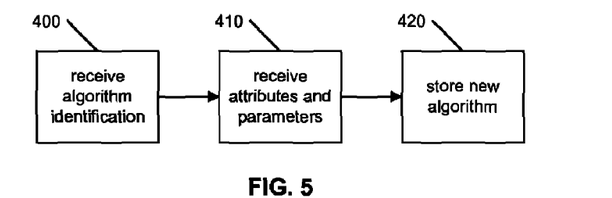
FIG. 5 is a flow diagram illustrating an example process for importing a remote image processing algorithm according to an embodiment of the present invention.

FIG. 5 is a flow diagram illustrating an example process for importing a remote image processing algorithm according to an embodiment of the present invention. In the first step 400, the execution manager receives the identification of an algorithm that is located on another server or computer that is remotely located and accessible via the network. Once the remote algorithm has been identified, in step 410 the execution manager receives any algorithm attributes and an identification of the parameters required by the algorithm during execution. These attributes and parameter requirements are preferably stored in a fashion that they correspond to the algorithm so that at a later time the execution manager may retrieve this information prior to execution of the algorithm, which will facilitate the collection of the parameter data prior to execution. Finally, in step 420, the new algorithm is stored along with its associated parameters and attributes.

Figure 6:
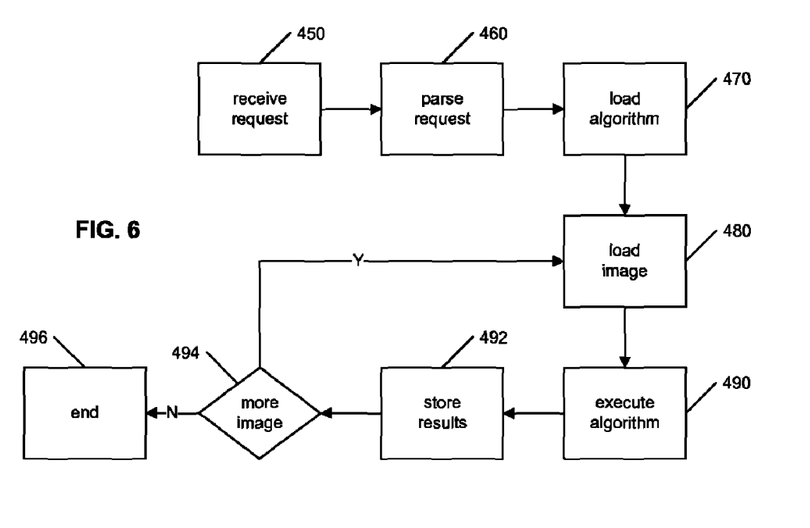
FIG. 6 is a flow diagram illustrating an example process for remotely executing an image processing algorithm according to an embodiment of the present invention.

FIG. 6 is a flow diagram illustrating an example process for remotely executing an image processing algorithm according to an embodiment of the present invention. Initially, in step 450, the execution manager receives a request from a remote user or program. Advantageously, the remote user may be an automated program that is developed to automate certain types of image processing on digital slides. Upon receipt of the request, in step 460, the execution manager parses the request to obtain information such as the particular algorithm to run, the identification of the digital slide (and optionally the sub-region thereof), as well as the parameter data.

Next, in step 470, the execution manager loads the algorithm and then also loads the image in step 480. At this point, the execution manager runs the algorithm to process the identified digital slide image, using the parameter data received in the request as necessary and in accordance with the particular algorithm. Any output generated by the running of the algorithm can advantageously be sent to a local output file or database, or it can be collected and the distributed remotely or locally or stored, as shown in step 492.

Digital slide images are very large, and it may be impractical to load an entire image in step 480. In such cases steps 480 and 490 can be repeated iteratively for multiple consecutive sub-regions of the digital slide image. Depending on the nature of the algorithm, it may be necessary or desirable to overlap the processed sub-regions, and then adjust the algorithm results. Accordingly, in step 494, the execution manager determines if there is more image data or additional image sub-regions to process. If so, the process loops back to step 480 where the next sub-region of the image is loaded. If there are no more sub-regions to process, then the execution manager can end the image processing, as illustrated in step 496.

Furthermore, some algorithms may benefit from multiple "passes" or recursive analysis/processing on an image. For example, a first pass (execution of the image processing instructions) can be made at low resolution (20×) to identify sub-regions of the image which require further analysis. Then a second pass (execution of the image processing instructions) can be made at high resolution (40×) to process and analyze just those sub-regions identified in the first pass. Advantageously, the algorithm results would reflect both passes (the sub-region identification and the output of the processing of the sub-regions).

Figure 7A:
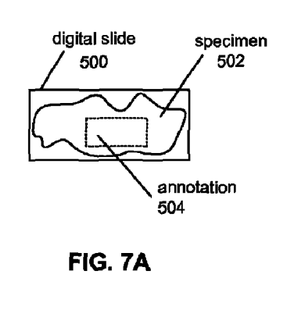
FIGS. 7A-7C are block diagram illustrating example digital slides with annotations and metadata masks according to embodiments of the present invention.
Figures 7B, 7C:
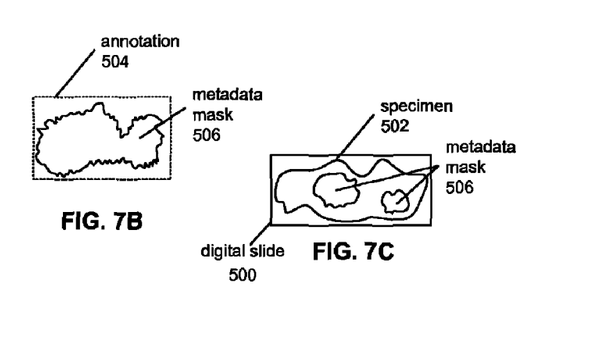

FIGS. 7A-7C are block diagram illustrating example digital slides 500 with annotations 504 and metadata masks 506 according to embodiments of the present invention. In FIG. 7A, the digital slide 500 includes an image of a specimen 502 that covers a substantial portion of the digital slide image. An optional annotation 504 is also shown that defines a sub-region of the digital slide image. For example, the sub-region defined by the annotation 504 may contain the desired image data to be analyzed with a particular algorithm. Although the annotation 504 is shown as a rectangle, which may be easily created by an operator with a pointing device or a computerized module, the annotation 504 may also be any other closed shape such as a circle, polygon, or free form shape. Open shapes that define a specific area of the specimen, e.g., by including an edge of the digital slide image 500 or an edge of the specimen 504 can also be used as an annotation 504.

FIG. 7B is an expanded view of the annotation 504. In one embodiment, the optional annotation is provided to initially define the area that includes the desired image data for processing by the algorithm. This advantageously reduces the amount of image data to be processed by the classifier. Once the classifier has processed the image data within the annotation 504, a metadata mask 506 is created that defines one or more regions of the digital slide 500 that include the desired image characteristic. The metadata mask 506 can be understood as either masking the non-desired image data from the digital slide image 500 or alternatively as providing the desired image data from the digital slide image 500. Importantly, application of the metadata mask 506 to the digital slide image 500 (or the annotation 504) results in the desired image data, which advantageously has an improved signal to noise ratio. The metadata mask can be applied relative to the whole digital slide image 500 or relative to the annotation 504.

In one embodiment, the metadata mask is created relative to the native resolution of the digital slide image 500. In such an embodiment, if the algorithm that is analyzing the desired image data calls for or is capable of analyzing image data at a different resolution, the digital slide image 500 is scaled to the different resolution and the metadata mask is also scaled to the different resolution so that it can be applied and provide the desired image data at the desired resolution to the algorithm for analysis.

In FIG. 7C, the classifier is applied to the entire digital slide image 500 and the result of the classifier processing is an metadata mask that includes two separate discrete areas of the digital slide image 500. Advantageously, a single metadata mask may include one or more separate and discrete regions of the digital slide image 500. This can be particularly advantageous for certain types of microscope slides and certain types of specimen that exhibit unconnected areas of interest that are desired to be processed and analyzed by the algorithm.

One particular advantage of the system using a classifier to create the metadata mask prior to analysis of the image data using the algorithm is that image processing algorithms are not complicated by the addition of image masking instructions. Furthermore, adding image masking instructions to the algorithm limits the applicability of the algorithm, for example to only the type of tissue to which the image masking instructions apply.

Additionally, significant efficiencies are also gained by applying the classifier to the digital slide image prior to analyzing the image data with the algorithm. For example, it may be desirable to analyze a single digital slide image that has multiple stains (e.g., three stains) with three separate algorithms. Using three separate classifiers on the digital slide image, the system is able to create three separate metadata masks, one for each stain. Accordingly, each of the three algorithms can be applied to the image data from each of the three metadata masks, resulting in nine total analyses using the three algorithms. Advantageously, the nine analyses are accomplished using only six developed modules. This is a significant improvement over conventional systems that would require nine separate algorithm modules to be developed to provide the same number of analyses. Another significant advantage is that an algorithm can be developed and validated one time and then used for a variety of different types of stains, tissues, etc., without having to develop and validate new algorithms for each separate type of stain, tissue, etc. A related advantage is that a classifier can also be developed and validated one time without having to be integrated into a plurality of separate algorithms and revalidated.

Figure 8:
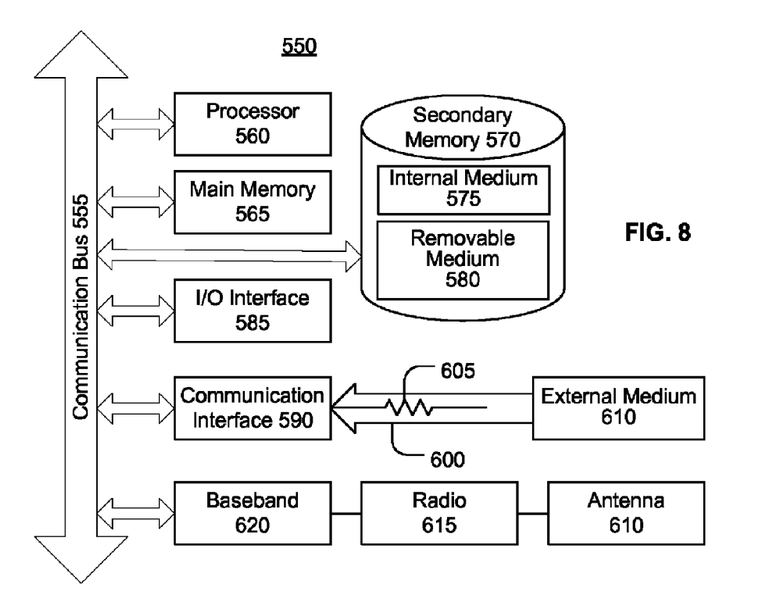
FIG. 8 is a block diagram illustrating an example wired or wireless processor enabled device that may be used in connection with various embodiments described herein.

FIG. 8 is a block diagram illustrating an example wired or wireless processor enabled device 550 that may be used in connection with various embodiments described herein. For example, the device 550 may be used in conjunction with, e.g., an algorithm server, a remote image server or a remote user station as previously described with respect to FIGS. 1 and 2. As will be clear to those skilled in the art, alternative processor enabled systems and/or architectures may also be used.

The processor enabled device 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the processor enabled device 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Processor enabled device 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the processor enabled device 550 for execution by the processor 560.

In alternative embodiments, secondary memory 570 may include other similar means for allowing computer programs or other data or instructions to be loaded into the processor enabled device 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the processor enabled device 550.

Processor enabled device 550 may also include a communication interface 590. The communication interface 590 allows software and data to be transferred between processor enabled device 550 and external devices (e.g. printers), networks, or information sources. For example, computer software or executable code may be transferred to processor enabled device 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/ point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication link. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the processor enabled device 550 to perform the various functions of the present invention as previously described.

In this description, the term "computer readable medium" is used to refer to any non-transitory computer readable storage media used to provide computer executable code (e.g., software and computer programs) to the processor enabled device 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the processor enabled device 550.

In an embodiment that is implemented using software, the software may be stored on a computer readable medium and loaded into processor enabled device 550 by way of removable medium 580, I/O interface 585, or communication interface 590. In such an embodiment, the software is loaded into the processor enabled device 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 620, a radio system 615 and a baseband system 610. In the communication device 550, radio frequency ("RF") signals are transmitted and received over the air by the antenna system 620 under the management of the radio system 615.

In one embodiment, the antenna system 610 may comprise one or more antennae and one or more multiplexors (not shown) that perform a switching function to provide the antenna system 620 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 610.

If the received signal contains audio information, then baseband system 610 decodes the signal and converts it to an analog signal. Then the signal is amplified and sent to a speaker. The baseband system 610 also receives analog audio signals from a microphone. These analog audio signals are converted to digital signals and encoded by the baseband system 610. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 620 where the signal is switched to the antenna port for transmission.

The baseband system 610 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the communication device 550 to perform the various functions of the present invention as previously described. For example, data storage areas 565 may include various software modules (not shown) that were previously described with respect to FIG. 2.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A computer implemented method for increasing the signal to noise ratio in digital pathology image data to be processed by a digital pathology image analysis algorithm, where one or more processors are programmed to perform steps comprising:
   receiving an identification of a digital slide image, a classifier associated with a desired characteristic, and an image analysis algorithm;
   analyzing the identified digital slide image using the identified classifier to generate a metadata mask that identifies digital slide image data corresponding to the desired characteristic;
   applying the metadata mask to the identified digital slide image to obtain image data from the identified digital slide image that includes the desired characteristic in accordance with the classifier; and
   processing the obtained image data that includes the desired characteristic in accordance with the classifier using the identified image analysis algorithm to generate an analysis of the digital slide image.

2. The method of claim 1, wherein the identification of a digital slide image identifies a sub-region of said identified digital slide image; and wherein the analyzing, applying, and processing steps are applied to said sub-region.

3. The method of claim 1, wherein the identified digital slide image has image data at a plurality of resolutions and wherein the analyzing step analyzes the identified digital slide image at the scanned resolution of the digital slide image.

4. The method of claim 3, wherein the metadata mask is generated relative to a resolution other than the scanned resolution of the digital slide image.

5. The method of claim 3, wherein the metadata mask is generated relative to the scanned resolution of the digital slide image.

6. The method of claim 5, further comprising scaling the metadata mask from the scanned resolution to a desired resolution, applying the metadata mask to the identified digital slide image at said desired resolution to obtain image data at the desired resolution that includes the desired characteristic in accordance with the classifier.

7. The method of claim 1 further comprising storing the metadata mask in a non-transitory computer readable medium.

8. A computer implemented method for increasing the signal to noise ratio in digital pathology image data to be processed by a digital pathology image analysis algorithm, where one or more processors are programmed to perform steps comprising:
   receiving a digital slide image identification;
   applying a first metadata mask to the identified digital slide image to determine first desired image data;
   applying a second metadata mask to the identified digital slide image to determine second desired image data;
   processing the first desired image data using a first algorithm to provide a first analysis of the digital slide image;
   processing the second desired image data using the first algorithm to provide a second analysis of the digital slide image;
   processing the first desired image data using a second algorithm to provide a third analysis of the digital slide image; and
   processing the second desired image data using the second algorithm to provide a fourth analysis of the digital slide image.

9. The method of claim 8, wherein the first metadata mask is obtained from a non-transitory computer readable medium.

10. The method of claim 8, wherein the second metadata mask is obtained from a non-transitory computer readable medium.

11. The method of claim 8, wherein the identified digital slide image is obtained from a non-transitory computer readable medium.

12. The method of claim 8, further comprising compiling the first, second, third and fourth analyses into an analysis of the digital slide image.

13. A technical system for increasing the signal to noise ratio in digital slide image data to be processed by a digital slide image analysis algorithm, the system comprising:
   a non-transitory computer readable medium for storing computer executable programmed modules;
   a processor communicatively coupled with the non-transitory computer readable medium for executing programmed modules stored therein;
   an image handler module stored in the non-transitory computer readable medium for applying a classifier to digital slide image data to generate a metadata mask that when applied to the digital slide provides digital slide image data corresponding to a desired characteristic for analysis using an image analysis algorithm;
   an image analysis algorithm stored in the non-transitory computer readable medium for analyzing the digital slide image data corresponding to the desired characteristic.

14. A system comprising at least one processor communicatively coupled with at least one non-transitory computer readable medium, wherein the processor is programmed to increase the signal to noise ratio in digital pathology image data to be processed by a digital pathology image analysis algorithm by:

receiving a digital slide image identification;

receiving a classifier identification, wherein the classifier is associated with a desired characteristic;

receiving an image analysis algorithm identification;

processing the identified digital slide image using the identified classifier to generate a metadata mask that when applied to the digital slide identifies digital slide image data corresponding to the desired characteristic;

storing the metadata mask;

providing image data corresponding to the desired characteristic from the identified digital slide in accordance with the classifier; and     processing the image data including the desired characteristic using the identified image analysis algorithm to generate an analysis of the digital slide image.

15. A non-transitory computer readable medium having stored thereon one or more sequences of instructions for causing one or more processors to perform the steps for increasing the signal to noise ratio in digital pathology image data to be processed by a digital pathology image analysis algorithm, the steps comprising:

receiving an identification of a digital slide image, a classifier associated with a desired characteristic, and an image analysis algorithm;

analyzing the identified digital slide image using the identified classifier to generate a metadata mask that identifies digital slide image data corresponding to the desired characteristic;

applying the metadata mask to the identified digital slide image to obtain image data from the identified digital slide image that includes the desired characteristic in accordance with the classifier; and     processing the obtained image data that includes the desired characteristic in accordance with the classifier using the identified image analysis algorithm to generate an analysis of the digital slide image.

\* \* \* \* \*